US00PP37346P3

(12) United States Plant Patent
Hansen

(10) Patent No.: US PP37,346 P3
(45) Date of Patent: Mar. 24, 2026

(54) ***HOSTA* PLANT NAMED 'Frog in My Throat'**

(50) Latin Name: ***Hosta* hybrid (Tratt.)**
Varietal Denomination: Frog in My Throat

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 136 days.

(21) Appl. No.: 18/831,120

(22) Filed: Jul. 25, 2024

(65) Prior Publication Data

US 2026/0033416 P1 Jan. 29, 2026

(51) Int. Cl.
*A01H 6/12* (2018.01)
*A01H 5/02* (2018.01)

(52) U.S. Cl.
USPC ..... Plt./353

(58) Field of Classification Search
USPC ..... Plt./353
CPC ..... A01H 6/00; A01H 5/02; A01H 6/12
See application file for complete search history.

*Primary Examiner* — Keith O. Robinson

(57) ABSTRACT

A new and distinct *Hosta* plant named 'Frog in My Throat' with medium-sized, rounded-mound habit of ovate to nearly cordate foliage. Leaves begin the season with a yellowish-green with greenish speckles, patches and streaks and mature to creamy-green to creamy in the center with variably-sized speckles, patches, and streaks of green and a green margin. The plant produces pale purple flared campanulate flowers on upright scapes well above the foliage beginning in mid-June and continuing for about three to four weeks.

2 Drawing Sheets

LATIN NAME AND VARIETY DENOMINATION OF THE PLANT

Botanical classification: *Hosta* hybrid (Tratt.).
Variety denomination: 'Frog in My Throat'.

STATEMENT REGARDING PRIOR DISCLOSURES UNDER 37 CFR 1.77(b)(6)

The first sale of 'Frog in My Throat' was to In the Country Garden & Gifts by Walters Gardens, Inc. on Apr. 30, 2024. Walters Gardens, Inc. obtained the new plant from the inventor. No plants of *Hosta* 'Frog in My Throat' have been sold in this country or anywhere in the world, nor has any disclosure of the new plant been made, more than one year prior the filing date of this application, and such sale or disclosure within one year was either derived directly or indirectly from the inventor and is therefore a 35 U.S.C. §102(b) exception.

BACKGROUND AND ORIGIN OF THE PLANT

The present invention relates to a new and distinct *Hosta* plant, *Hosta* 'Frog in My Throat', hereinafter also referred to as the new plant or just the cultivar name, 'Frog in My Throat'. *Hosta* 'Frog in My Throat' was discovered by the inventor spring of 2022, at a wholesale perennial nursery greenhouse in Zeeland, Michigan, USA as a whole plant mutation in a tissue-cultured batch of 'Emperor's New Clothes' U.S. Plant Pat. No. 34,312. The new plant was approved for final selection in the spring of 2024. The new plant has been asexually propagated by division at the same nursery in Zeeland, Michigan, USA since 2023 with the resultant asexually propagated plants having retained all the same traits as the original plant. *Hosta* 'Frog in My Throat' is stable and reproduces true to type in asexual reproduction.

BRIEF SUMMARY OF THE PLANT

There are nearly 7,000 registered *Hosta* cultivars with The American *Hosta* Society, which is the International Cultivar Registration Authority for the genus *Hosta* along with a similar number of unregistered cultivars. The nearest comparison varieties are: 'Allegan Fog' (not patented), 'Spilt Milk' (not patented), 'London Fog' (not patented), 'Northem Mist' (not patented), 'Revolution' (not patented), 'Lakeside Elfin Fire' (not patented), 'Lakeside Wizzit' (not patented), 'Masquerade' (not patented) and 'Gunther's Prize' (not patented).

'Allegan Fog' has a smaller habit and leaves are smaller with a dark green margin and smaller green speckles in the creamy white center. 'Spilt Milk' has broader blue-green foliage. that has linear speckles or short streaks of white. 'London Fog' has a smaller habit with narrower more wavy foliage having smaller speckles of green in a greenish-white leaf. 'Northern Mist' has a slightly larger habit with more bullate foliage that has a wide deep-green margin and green speckles in a creamy-white center. 'Revolution' has a smaller habit with flatter more lustrous foliage that has a wide deep-green margin and green speckles in a creamy-white center and shorter leaf blades that have a thicker texture. 'Lakeside Elfin Fire', 'Lakeside Wizzit', and 'Masquerade' are all significantly smaller in habit and leaf size, the leaves are narrower and more lanceolate-shaped. Each of the above have speckles that are smaller than the new plant.

'Gunther's Prize' has a large yellowish leaf with large chartreuse to medium green speckles and streaks, the flower stalks are more arching to nearly horizontal, the flower shape is not as widely flared, and the flower color is a deeper lavender purple in the center of the tepals.

The parent of the sport, 'Emperors New Clothes', has leaves with a yellowish-green background and large dark green patches, streaks, or speckles throughout the entire leaf and without the solid dark green margin.

*Hosta* 'Frog in My Throat' is distinct from the *Hostas* listed above and all other cultivars known to the hybridizer by the following combined traits:

1. Medium-sized, rounded-mound plant habit with outwardly-projecting, glaucous foliage becoming dull to slightly shiny on top;
2. Foliage is ovate to nearly cordate that is wavy when young;
3. Foliage is variegated, emerging yellowish green in the center with green speckles, patches, and streaks, and a green margin;
4. Foliage becomes creamy-green to creamy in the center in the late season from the with green patches and streaks, and a green margin;
5. Pale purple, flared, campanulate flowers, well above the foliage, densely arranged, on numerous arching scapes beginning in mid-June for about three to four weeks.

BRIEF DESCRIPTION OF THE DRAWINGS

The photographs of the new plant demonstrate the overall appearance of a three-year-old plant, including the unique traits of 'Frog in My Throat'. The colors are as accurate as reasonably possible with color reproductions. Ambient light spectrum, temperature, source and direction may cause the appearance of minor variation in color.

DETAILED BOTANICAL DESCRIPTION

Figure 1:
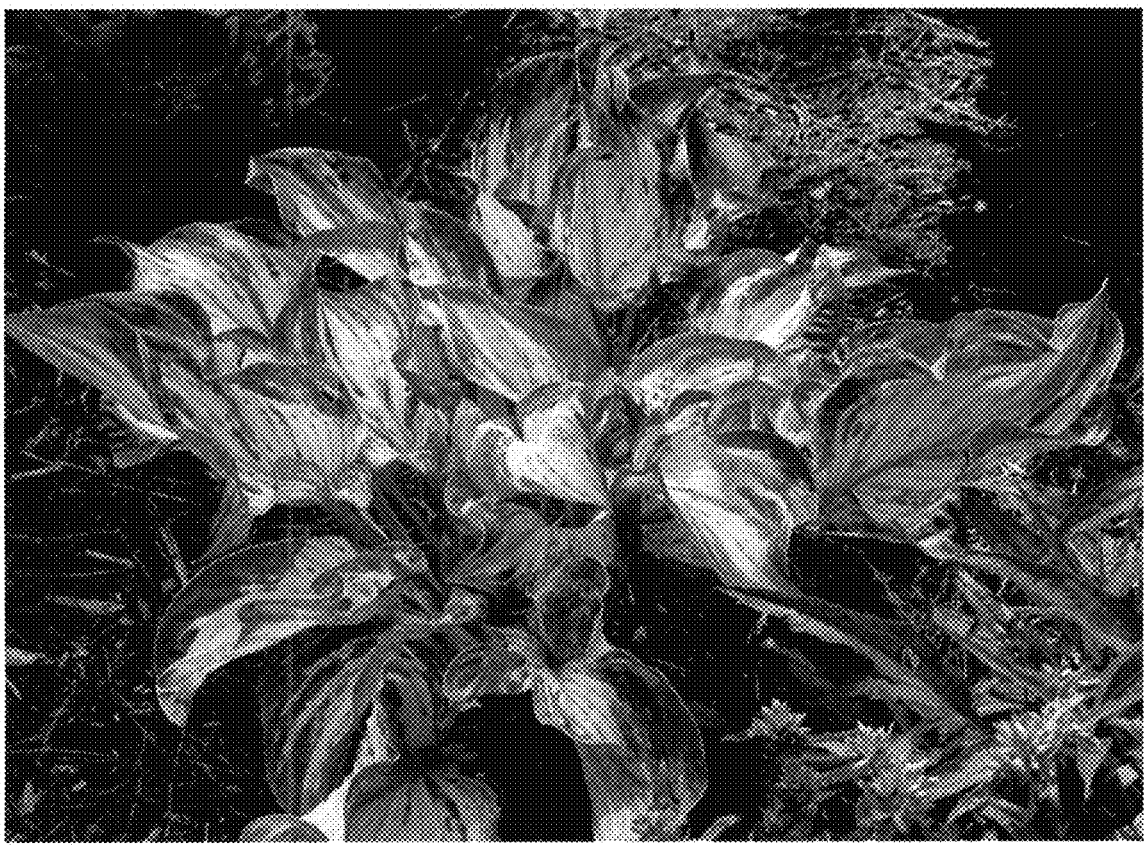
FIG. 1 shows a plant grown in a shaded display garden in early summer.
Figure 2:
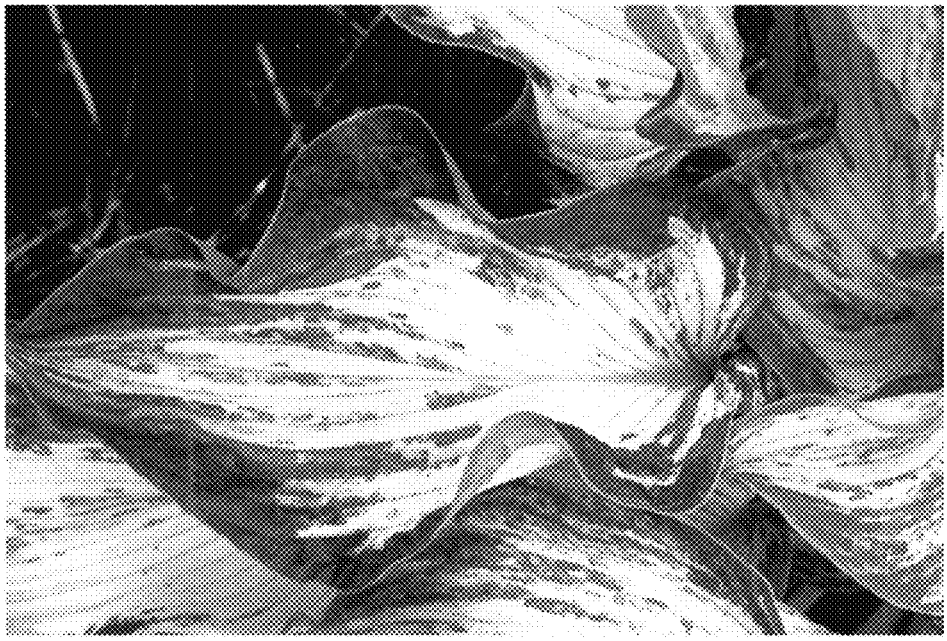
FIG. 2 shows a close-up of a leaf in mid-season prior to flowering.
Figure 3:
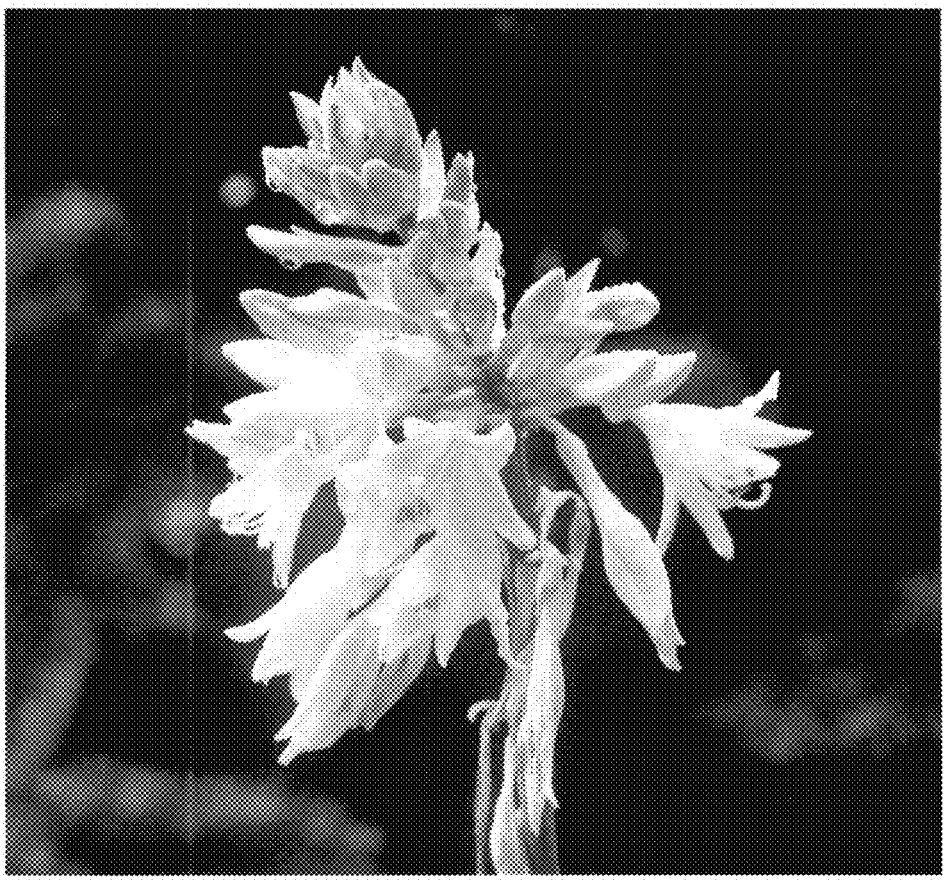
FIG. 3 shows a flowering scape with open flowers, buds, and floral bracts.

The following descriptions and color references are based on the 2015 edition of The Royal Horticultural Society Colour Chart except where common dictionary terms are used. The new plant, *Hosta* 'Frog in My Throat', has not been observed under all possible environments. The phenotype may vary slightly with different environmental conditions, such as temperature, light, fertility, moisture and maturity levels, but without any change in the genotype. The following observations and size descriptions are of a three-year-old plant in a shaded trial garden in Zeeland, Michigan with supplemental water and fertilizer.

Botanical classification: *Hosta* hybrid;

Parentage: The parent plant is 'Emperor's New Clothes';

Propagation: Garden division;

Growth rate: Moderate to rapid;

Crop time: About 2 to 3 months to finish during the summer in a one-liter container from rooted tissue culture plantlet;

Rooting habit: Normal, fleshy, lightly branching;

Root color: Variable, nearest RHS 164D to RHS 158D depending on soil type;

Plant shape and habit: Hardy herbaceous perennial with basal rosette of mostly outwardly pointed leaves emerging from rhizomes producing a large symmetrical rounded-mound of leaves;

Plant size: Foliage height to about 45 cm from the soil line to the top of the leaves and about 90 cm wide at the widest point slightly above the soil line;

Foliage description: Ovate to cordate; glabrous, top surface begins season slightly glaucous becoming dull matte surfaced to slightly shiny, and bottom surface is glaucous and tends to stay through most of the season; margin entire and moderately coarsely sinuate; narrowly acute and slightly twisted apex; attenuate to cordate base; with slightly impressed veins; slightly to moderately folded; not significantly bullate;

Leaf blade size: To about 24 cm long and 17 cm wide; width to length ration of about 1:1.5 but typically becomes broader with maturity; with patches and speckles of various sizes of between 0.5 mm diameter and 6.0 cm long and 1.5 cm across; margin width inconsistent, to about 20 mm adaxial and abaxial;

Leaf blade color: Early season and shortly after emerging variable, adaxial center between RHS 145D and RHS 150D with irregularly-sized and shaped patches and speckles of variable green colors comprising RHS NN137A, N138A, RHS 144A and between RHS N138D and RHS 189B, margin nearest RHS N138A, abaxial center nearest RHS 150D with irregular patches and speckles comprising RHS 191C and RHS N138D; late summer to early fall adaxial center near white between RHS NN155C and RHS NN155D having a minute speckling of nearest RHS 137A with irregular patches and streaks of variable green colors comprising nearest RHS 144A, RHS 137A, and between RHS N138A and RHS 189A, late summer to early fall abaxial center between RHS 157C and RHS 155C with speckles or variably-sized patches of comprising nearest RHS N138B, RHS 189B, and RHS 194B, and margin nearest RHS N138B;

Petiole: Glabrous; slightly glaucous; concavo-convex; mostly straight from base of plant to leaf blade; to about 28 cm long and at base 22 mm across about 5 mm above the soil;

Petiole color: Early season adaxial margin between RHS 138B and RHS N138C and center nearest RHS 145B with minute speckles less than 1 mm nearest RHS 139B, abaxial margin nearest RHS 138C and center nearest RHS 145C; late summer to fall adaxial margin nearest RHS 137C and center nearest RHS 145C, abaxial margin nearest RHS 137C and center nearest RHS 145D;

Veins: Parallel; only lightly impressed adaxial, slightly costate abaxial; to 14 pairs with one midrib;

Veins color: Adaxial between RHS 145B and RHS 145A; abaxial between RHS N148C and RHS 145A, with abaxial midrib nearest RHS 145D;

Flower description—

Buds: One day prior to opening clavate with acute apex gradually tapering to a long thin corolla tube and rounded base; nearest RHS 91D in basal portion and RHS 92D at middle and apex; to about 45 mm long, and 9 mm wide at the broadest portion, corolla tube portion to about 16 mm and 3 mm diameter; sizes decreasing distally;

Bud color: Nearest RHS 91D at base and RHS 92D at middle and apex;

Inflorescence: Cylindrical; glabrous; 28 to 34 per scape; tightly arranged with about 6 to 8flowers per 1 cm centimeter of scape in some areas and spaced 1 cm apart in other areas; to about 90 cm long and 7 mm diameter at base;

Flowers: Single; perfect; incomplete; funnelform; about 35 mm wide and 48 mm long to exserted stigma, size decreasing distally;

Flower lasting: Remain open for a normal period, usually one to two days on or cut from plant; Flower season: Scapes remain effective from mid-June into mid-July for about three to four weeks in Zeeland, Michigan;

Flower fragrance: None detected;

Tepal: Two nearly identical sets of three fused at the proximal one-half; acute apex; margins entire; approximately 46 mm long and 10 mm wide (outer set) 47 mm long and 12 mm wide (inner set);

Tepal color: Adaxial outer and inner sets nearest RHS 85D in the distal half center with veins nearest RHS 85C and margins nearest RHS NN155D and a transparent edge of about 1 mm wide on the inner set, with the fused corolla tube between RHS NN155D and RHS 85D; abaxial distal half between RHS 85D and RHS NN155D with veins nearest RHS 85D and fused corolla tube between RHS NN155D and RHS 85D with an undertone of nearest RHS 146D;

Pedicel: Cylindrical; glaucous becoming lustrous; approximately 11 mm long, 1.5 mm wide; attitude mostly outwardly;

Pedicel color: Distally nearest RHS NN155A and proximally nearest RHS 146C;

Peduncle: Cylindrical; glaucous; usually one per division, erect to slightly arching, about 7 mm diameter at base, average 80 cm tall;

Peduncle color: Nearest RHS N138B;

Gynoecium: Single; superior; about 45 mm long;

Style: About 37 mm long, 1 mm diameter, curled upward at distal 8 mm; color base nearest RHS 145D, nearest RHS NN155D in distal 10 mm;

Stigma: 1.5 mm diameter; puberulent; color nearest RHS NN155D;

Ovary: Fluted longitudinally; ellipsoidal; to about 6 mm long and 3 mm across; color nearest RHS 145A;

Androecium: Six;

Filaments: Six; about 0.5 mm in diameter and 44 mm long, curving upward the last 8 mm; nearest RHS NN155D distally and between RHS 145D and RHS NN155D proximally;

Anthers: Oblong; dorsifixed; longitudinal; about 4 mm long and 2 mm wide; prior to pollen dehiscing dorsal nearest RHS 13A and ventral between RHS 13C and RHS 13B, when pollen dehisced dorsal color between RHS N187C and lighter than RHS N77D, ventral between RHS 177A and RHS 177B;

Pollen: Elliptical, less than 0.1 mm long, nearest RHS 13B;

Floral bracts: Subtending one or more flowers; lanceolate; widest at base and tapering to acute apex; truncate sessile base; margin entire; protruding upward about 80-degree angle away from scape; average about 17 mm long and 7 mm wide in middle; decreasing distally and increasing proximally in both length and width;

Floral bract color: Young bracts adaxial and abaxial between RHS 76B and RHS 147D prior to flower opening; after flower opening adaxial and abaxial drying to nearest RHS 199D;

Scape bract: Typically, one or two below flowers; lanceolate; divergent from scape by about 45-degrees; glaucous adaxial and abaxial; to about 70 mm long and 15 mm wide;

Scape bract color: Adaxial and abaxial margins nearest RHS 138A, centers between RHS 155A and RHS 157A with small flecks of nearest RHS 138B, and intermediate region between margins and centers comprising RHS 145B and between RHS 145A and RHS N144A;

Fruit: Rare; tri-valved dehiscent capsule; oblong; apiculate apex and truncate base; lightly furrowed; about 22 mm long and 5 mm diameter; color as developing nearest RHS 137A, if maturity reached between RHS 164C and RHS 164D;

Seed: Typically, few per capsule under pollination attempts; endospermic; flattened-elliptic wing surrounding embryo situated toward one end of ellipse; up to 5 mm long and 1.5 mm wide and 1 mm thick at embryo; color nearest RHS 202A;

Disease tolerance and resistance: *Hosta* 'Frog in My Throat' has not shown any resistance or susceptibility to pests and diseases common to *Hostas*.

Growth: The new plant grows best and shows its best coloration with plenty of moisture, adequate drainage and light shade, but is able to tolerate some drought when mature.

Hardiness: At least from USDA zone 3 through 9.

It is claimed:

1. A new and distinct ornamental *Hosta* plant named 'Frog in My Throat' as herein described and illustrated.

* * * * *